(12) United States Patent
Freyberg et al.

(10) Patent No.: US 7,582,725 B2
(45) Date of Patent: Sep. 1, 2009

(54) AGENTS, WHICH INHIBIT APOPTOSIS IN CELLS THAT ARE INVOLVED IN WOUND HEALING

(75) Inventors: Mark Freyberg, Darmstadt (DE); Peter Friedl, Gross-Umstadt (DE); Dirk Kaiser, Eppertshausen (DE)

(73) Assignee: Dermatools Biotech GmbH, Darmstadt (DE)

( * ) Notice: Subject to any disclaimer, the term of this patent is extended or adjusted under 35 U.S.C. 154(b) by 65 days.

(21) Appl. No.: 10/469,126

(22) PCT Filed: Feb. 21, 2002

(86) PCT No.: PCT/EP02/01828

§ 371 (c)(1), (2), (4) Date: Aug. 25, 2003

(87) PCT Pub. No.: WO02/083160

PCT Pub. Date: Oct. 24, 2002

(65) Prior Publication Data

US 2004/0101526 A1    May 27, 2004

(30) Foreign Application Priority Data

Feb. 26, 2001    (DE) .............................. 101 09 136

(51) Int. Cl.
*C07K 2/00* (2006.01)
*C07K 5/00* (2006.01)
*C07K 1/00* (2006.01)
*A61K 38/00* (2006.01)

(52) U.S. Cl. ................. 530/300; 530/329; 530/350; 530/351; 530/380; 514/2; 514/17

(58) Field of Classification Search ............... 435/69.1, 435/325, 375, 455; 424/9.1, 9.2; 514/2
See application file for complete search history.

(56) References Cited

U.S. PATENT DOCUMENTS

| | | | | |
|---|---|---|---|---|
| 5,627,265 A |  | 5/1997 | Frazier et al. ............... | 530/350 |
| 6,562,958 B1 | * | 5/2003 | Breton et al. ............... | 536/23.7 |
| 6,605,709 B1 | * | 8/2003 | Breton ....................... | 536/23.1 |
| 2005/0208558 A1 | * | 9/2005 | Venter et al. ................ | 435/6 |

FOREIGN PATENT DOCUMENTS

| | | |
|---|---|---|
| DE | 199 52 960 A1 | 5/2001 |
| EP | 903 149 A1 | 3/1999 |
| EP | 1 005 873 A1 | 6/2000 |
| WO | WO 99/43787 A2 | 9/1999 |
| WO | WO 99/43787 A3 | 9/1999 |
| WO | WO 01/33218 A1 | 5/2001 |

OTHER PUBLICATIONS

Diegelmann et al, Frontiers in Bioscience 9, 283-289, 2004.*
Bornstein JCI 107(8):929-934, 2001.*
Armstrong et al; Matrix Biology 22:63-71, 2003.*
Gao et JBC 135(2):533-544, 1996.*
AN:AAV45504 (WO96402285), 1996.*
"Integrin-Associated Protein and Thrombospondin-1 as Endothelial Mechanosensitive Death Mediators", Freyberg et al., Biochemical and Biophysical Research Communications 271, 2000, pp. 584-588.
International Search Report in PCT/EP02/01828 dated Dec. 9, 2002.
International Preliminary Examination Report in PCT/EP02/01828 dated Feb. 12, 2003.
"Apparatus for Subjecting Living Cells to Fluid Shear Stress", Bussolari et al., Rev. Sci. Instrum. 53(12), Dec. 1982, pp. 1851-1854.
"Use of Fluo-3 to Measure Cytosolic $Ca^{2+}$ in Platelets and Neutrophils", Merritt et al., Biochem. J. 269, 1990, pp. 513-519.
"Overview: Mechanisms of Apoptosis", Cohen, Immunology Today, vol. 14, No. 3, 1993, pp. 126-136.
"A 50-kDa Integrin-Associated Protein is Required for Integrin-Regulated Calcium Entry in Endothelial Cells", Schwartz et al., The Journal of Biological Chemistry, vol. 268, No. 27, 1993, pp. 19931-19934.
Peptidmimetica—Maßgeschneiderte Enzyminhibitoren, Gante, Angew. Chem 106, 1994, pp. 1780-1802.
"Zell-Und Gewebekultur", Lindl et al., Laboratory Manual, cover page only, 1994.
"Case Histories of Peptidomimetics: Progression from Peptides to Drugs", Adang et al., Recl. Trav. Chim. Pays-Bas 113, 1994, pp. 63-78.
"Structural and Functional Aspects of RGD-Containing Cyclic Pentapeptides as Highly Potent and Selective Integrin $\alpha_v \beta_3$ Antagonists", Haubner et al., J. Am Chem. Soc. 118, 1996, pp. 7461-7472.
"Optimizing Oral Absorption of Peptides Using Prodrug Strategies", Borchardt, Journal of Controlled Release 62, 1999, pp. 231-238.
"Ring-Closing Metathesis of Olefinic Peptides: Design, Synthesis, and Structural Characterization of Macrocyclic Helical Peptides", Blackwell et al., J. Org. Chem. 66, 2001, pp. 5291-5302.

* cited by examiner

*Primary Examiner*—Sumesh Kaushal
(74) *Attorney, Agent, or Firm*—Marshall, Gerstein & Borun LLP

(57) ABSTRACT

The invention relates to the use of substances as a fundamental constituent in wound healing agents. The invention is characterised in that said substances bond to either IAP and/or integrin $\alpha_v \beta_3$ and/or thrumbospondin-1 in such a way that the bond between thrumbospondin-1 and IAP and/or integrin $\alpha_v \beta_3$ is inhibited.

21 Claims, 2 Drawing Sheets

AGENTS, WHICH INHIBIT APOPTOSIS IN CELLS THAT ARE INVOLVED IN WOUND HEALING

This is the U.S. national phase of International Application No. PCT/EP02/01828 filed Feb. 21, 2002, the entire disclosure of which is incorporated herein by reference.

BACKGROUND OF THE INVENTION

1. Field of the Invention

The present invention relates to agents which have an antiapoptotic effect on cells involved in wound healing. In particular, the present invention relates to the use of substances which bind either to IAP and/or to integrin $\alpha_v\beta_3$ and/or to thrombospondin 1 in such a way that the binding between thrombospondin 1 and IAP and/or integrin $\alpha_v\beta_3$ is inhibited, thus reducing the rate of apoptosis of cells associated with wound healing, for producing medicaments which are suitable for the treatment of traumatic conditions, preferably chronic wounds. Preferred exemplary embodiments encompass the amino acid sequences depicted in SEQ ID Nos 1-11, and peptidomimetics derived therefrom. The present invention further relates to cells having a significantly reduced rate of apoptosis, it being possible to use these cells preferably as constituent of a so-called artificial skin which has already been described in the prior art, and the skin being mechanically tensioned before application of this skin to the wound, and the corresponding cells preferably being treated additionally with the agents of the invention.

2. Description of Related Technology

The process of wound healing consists of three phases during which the injured tissue is repaired and is thus regenerated, after which the new tissue becomes manifest as scar.

These three phases are classified in the following way:
(a) inflammatory phase which starts after 0 to 3 days
(b) a subsequent cellular proliferation phase of 3 to 12 days, and
(c) a restorative phase of 3 days to about 6 months.

In the inflammatory phase, inflammatory cells, mainly neutrophils, collect at the wound site, followed by lymphocytes, monocytes and even later macrophages.

During the proliferation phase, the so-called granulation tissue (highly vascularized connective tissue which forms during the healing of wounds, ulcers inter alia) is formed in the injured area. An important part is played in this by, in particular, fibroblasts and epithelial cells (re-epithelization), besides other cell types. The fibroblasts produce the collagen which is important for wound healing.

Ascorbic acid (vitamin C) is essential for the formation of collagen. It has already been shown in several investigations that the use of ascorbic acid activates the reduced proliferative activity and the collagen synthetic activity of aged skin fibroblasts, and therefore wound healing is improved. However, the mode of action has not been shown, but inter alia an involvement of vitamin C in lipid oxidation processes is described.

During the re-epithelization, the epithelial cells proliferate and migrate from the edges of the wound into the tissue. It has been possible to show in this connection that re-epithelization can be promoted by wound dressings which represent a moisture barrier.

The concluding phase of wound healing is characterized by the replacement of the granulation tissue by collagen and elastin fibers and the devascularization of the granulation tissue (i.e. formation of scar tissue). Recent studies have moreover shown that topical application of antioxidants such as alpha-tocopherol reduces scar formation and normalizes blood coagulation during therapy.

Fibroblasts and epithelial cells in particular therefore play an important part in wound healing. The low proliferation activity of the fibroblasts and the small number thereof impedes favorable wound healing. In many cases there is use, besides antiinflammatory substances, also of substances such as growth factors which are intended to enhance the proliferation abilities or the synthetic activity of the cells involved.

Apoptosis (synonym: programmed cell death) is an irreversible process. An apoptotic cell inevitably dies. Apoptotic fibroblasts have been suggested to have a negative role in wound healing, but no way has yet been proposed for having a beneficial influence on the rate of apoptosis of fibroblasts during wound healing by bringing particular medicaments, i.e. molecular remedies, into contact with the fibroblasts.

European patent application EP-A-0 903 149 describes a method for identifying apoptosis-inducing substances in immune cells. It was shown that substances which bind to the integrin-associated protein (IAP or CD 47) on the surface of immune cells may have the ability to induce apoptosis. The mechanisms of action were not described.

It has already been proposed that IAP is involved in the formation of a specific calcium channel (Schwartz, M. A. et al., Journal of Biological Chemistry, 268:27, 19931-19934). No mention was made of a role of this hypothetical calcium channel in the induction of apoptosis.

The applicant's international patent application WO 01/33218 A1 of earlier priority, the full contents of which are incorporated in the present application by reference, describes a method for identifying apoptosis-inhibiting substances and the use of such substances for producing medicaments for the treatment of vascular disorders and as active principle in a pharmaceutical preparation for the treatment of vascular disorders. A use of such substances for producing medicaments for promoting wound healing or as active principle of a pharmaceutical preparation for the treatment of wounds was not described.

One of the most modern approaches to the treatment of chronic wounds is the use of a so-called living skin as skin substitute or wound-covering means. There has already been a large number of patent applications in this area. Mention may be made here representatively to EP 1 005 873 of Isotis N.V. or the international patent application WO 99/43787 of Advanced Tissue Sciences Inc. The principle of the production of such an artificial skin is to grow either autologous or heterologous cells (skin cells) on a biocompatible membrane and then use this artificial skin as remedy. However, it has not previously been described that it is beneficial or necessary to inhibit the apoptosis of the cells used in order to ensure a more favorable progress of the healing. Neither stretching of the artificial skin nor the addition of anti-apoptotic agents is proposed. A negative effect of apoptosis on the progress of healing is not discussed in these patent applications and is not made obvious to the skilled worker.

A healing influence of chronic traumatic conditions or large-area and/or deep wounds, like those frequently occurring in burn injuries, in particular is possible at present, despite the prior art mentioned, only with difficulty.

There is thus still a great need in the art for improved means which beneficially influence wound healing, and in particular also the healing of chronic wounds or large-area wounds or burn injuries of the skin.

DETAILED DESCRIPTION

The present invention is therefore based on the object of providing substances and/or agents which are suitable for producing a medicament or a means for the treatment of traumatic conditions and/or burn injuries.

This is achieved, as are other not explicitly mentioned objects which, however, can be deduced or inferred directly from the relationships discussed in the introduction, according to the invention. Expedient modifications of the use according to the invention are described.

The object is achieved in particular by the use of substances which bind either to IAP and/or to integrin $\alpha_v\beta_3$ and/or to thrombospondin 1 in such a way that the binding between thrombospondin 1 and IAP and/or integrin $\alpha_v\beta_3$ is inhibited, and which reduce the rate of apoptosis of cells associated with wound healing, for producing medicaments which comprise as active ingredient at least one such substance, and which are employable for the treatment of wounds, in particular for the treatment of chronic wounds and/or burn injuries.

A medicament for the treatment of said wound injuries can be produced by initially carrying out an identification cation method of stages (i) to (v), wherein:
(i) cells which express both IAP and the integrin $\alpha_v\beta_3$ are cultured,
(ii) the cells are caused to produce an apoptosis-inducing substance, and/or a substance or substances inducing apoptosis is/are added,
(iii) a test substance as claimed in any of claims 5 to 9 added,
(iv) the rate of apoptosis is measured, and
(v) test substances which bring about a reduced rate of apoptosis are selected, and then
(vi) the test substances identified in this way (identificates) are mixed with a pharmaceutically suitable carrier.

The substances (identificates) which can be used according to the invention particularly preferably inhibit the apoptosis of fibroblasts and/or epithelial cells.

The present invention additionally preferably encompasses medicaments which comprise as active ingredient one such substance and one or more, optionally different fibroblast growth factors, such as, for example, basic fibroblast growth factor (bFGF), and which are employable for the treatment of wounds, and in particular for the treatment of chronic wounds and/or burn injuries.

The invention additionally encompasses preferably the use of these substances for the treatment of traumatic conditions, in particular for the treatment of chronic wounds.

The object of the invention is achieved in particular by the provision of substances which comprise peptides having one of the amino acid sequences depicted in SEQ ID Nos 1 to 11.

A preferred exemplary embodiment of the present invention comprises in this connection apoptosis-inhibiting substances which include amino acid sequences of the general formula (1):

R-A1-Y-V-V-M, where A1 is A, D, E, G, M, N, T, W or Y, or pharmaceutically acceptable salts of these substances.

For the purposes of the present invention, the internationally customary one-letter code for amino acids is used, and thus A is alanine (Ala), C is cysteine (Cys), D is aspartic acid (Asp), E is glutamic acid (Glu), F is phenylalanine (Phe), G is glycine (Gly), L is leucine (Leu), M is methionine (Met), N is asparagine (Asn), P is proline (Pro), R is arginine (Arg), S is serine (Ser), T is threonine (Thr), V is valine (Val), W is tryptophan (Trp) and Y is tyrosine (Tyr).

In a particularly preferred aspect, the present invention therefore relates to apoptosis inhibiting substances, preferably proteins or peptides, which comprise one of the peptide sequences shown in SEQ ID No. 1 to SEQ ID No. 11, or the corresponding pharmaceutically acceptable salts thereof.

The present invention further relates to the use of the substances of the invention, preferably proteins or peptides comprising at least one of the amino acid sequence depicted in SEQ ID No. 1 to SEQ ID No. 11 for producing medicaments, in particular for producing medicaments for the treatment of traumatic conditions, and very particularly preferably in this connection chronic wounds or severe burn injuries.

Surprisingly, the inventors have shown that peptides comprising an amino acid sequence represented by formula (1) inhibit apoptosis to an extremely great extent. These peptides are outstandingly suitable in particular for inhibiting TSP-1 induced apoptosis.

The following peptides/peptide sequences are provided as very particularly preferred exemplary embodiments of the present invention:

```
 1.  R-A-Y-V-V-M              (SEQ ID No.  1)
 2.  R-W-Y-V-V-M              (SEQ ID No.  2)
 3.  R-Y-Y-V-V-M              (SEQ ID No.  3)
 4.  R-E-Y-V-V-M              (SEQ ID No.  4)
 5.  K-R-A-Y-V-V-M-W-K-K      (SEQ ID No.  5)
 6.  K-R-E-Y-V-V-M-W-K-K      (SEQ ID No.  6)
 7.  R-G-Y-V-V-M              (SEQ ID No.  7)
 8.  R-M-Y-V-V-M              (SEQ ID No.  8)
 9.  R-T-Y-V-V-M              (SEQ ID No.  9)
10.  R-N-Y-V-V-M              (SEQ ID No. 10)
11.  R-D-Y-V-V-M              (SEQ ID No. 11)
```

In a further preferred embodiment of the present invention, cells involved in wound healing, preferably fibroblasts or epithelial cells, are cultivated as a so-called artificial skin already known in the art, and the latter is used according to the invention as wound-healing means, in which case this artificial skin is, after growth of the cells, mechanically tensioned and/or in which case the corresponding cells are treated, before or after application of the artificial skin to the site of the wound, with the agents of the invention, and where the proportion of apoptotic cells in the total number of cells can be reduced by at least 10%, preferably by at least 50%, particularly preferably by at least 75% and very particularly preferably by at least 90%, compared with an artificial skin which has not been mechanically tensioned and has not been treated with the agents of the invention.

This entails this skin being stretched, preferably after growth of the cells on the biocompatible membrane or immediately before application of the skin to the wound, by 10-90%, and application of the agent of the invention preferably 8-24 h after the stretching.

Surprisingly, the aforementioned inventors have shown that the binding of thrombospondin-1 (TSP-1) to IAP and/or the integrin $\alpha_v\beta_3$ induces apoptosis in fibroblasts (examples 6 and 7). The corresponding investigations were carried out on MRC-5 fibroblasts (ATCC No.: CCL-171). The rate of apoptosis is determined as shown in example 3.

It was additionally possible, surprisingly, to show that the TSP-1 is produced by the fibroblasts themselves, and thus the apoptosis is self-induced or spontaneous (example 8 and 9). These investigations were carried out in conventional static cell cultures. The latter are distinguished by the absence of flows in the cell culture medium. However, it was possible unexpectedly to show that TSP-1 is not produced by fibroblasts in a dynamic cell culture (cultivation in the cone and plate shear apparatus, see example 1), i.e. under conditions with which the cells are confronted by a flowing cell culture medium, and apoptosis occurs to only a very small extent or not at all in this cell culture (example 5 and 8). This was highly surprising also because it cannot be assumed that fibroblasts are exposed under natural conditions to shear stresses caused by liquid flows.

Supplementation of fresh medium with TSP-1 causes an increase in spontaneous apoptosis in statically cultivated fibroblasts (example 6). This increase corresponds approximately to the effect of statically conditioned medium (example 5). The term conditioned medium means here a cell culture medium which has previously already been used to cultivate other cells. This medium is distinguished by the fact that soluble mediators, e.g. growth factors, hormones, etc., which are produced by cells during their cultivation, are dissolved therein. This result shows that statically conditioned medium has the ability to induce apoptosis via a mediator such as TSP-1. The production of conditioned medium is explained in example 2.

It was possible to show by the use of an anti-TSP-1 antibody which binds to and thus neutralizes TSP-1 that TSP-1 is the mediator of the apoptosis of fibroblasts (example 6). The effect of added TSP-1 can be suppressed, just like the effect of statically conditioned medium, by addition of a polyclonal antiserum against TSP-1 and by addition of a monoclonal anti-TSP-1 antibody (example 6).

The TSP-1 secretion rates were determined for dynamic and static post-confluent cultures (example 8 and 9).

The term "static cell culture (conditions)" means here a cultivation of cells under conditions with which invariable, i.e. consistently directed, laminar flows do not occur in the cell culture medium surrounding the cells. The "static cell culture conditions" in the sense used herein thus include cell culture conditions under which turbulent or variable laminar flows, that is to say, for example, those with changing directions of flow or even with reversal of flow, occur. The term "dynamic cell culture (conditions)" means here cell culture conditions with which only consistently directed, laminar flow conditions prevail in the cell culture medium, i.e. cell culture conditions like those which can be achieved in the prior art for example with the aid of cultivation in a cone and plate shear apparatus (see example 1). It is clear that in the in vivo situation liquid flows do not occur with fibroblasts, because the connective tissue, in which the fibroblasts are chiefly located, is not a liquid-filled compartment.

The shear stresses acting on the cultivated cells in the cell culture vary with the flow conditions. A consistently directed laminar flow results in a shear stress which is greater than 0.001 dyn/cm$^2$ and whose vector sum is greater than under variable flow conditions with changing directions of flow. Static cell culture (conditions) are distinguished by distinctly smaller (<0.001 dyn/cm$^2$) or absolutely no stress. Dynamic cell cultures show shear stresses of >0.001 dyn/cm$^2$ or a Reynolds number of >0.1. Turbulent flows may occur at Reynolds numbers of >200 (–1 000) (depending on the geometry of the flow chamber) and, like static or variable flow conditions, no longer have a protective character in relation to the induction of apoptosis. Various cultivation methods were used for investigations which led to the present invention. These are described in example 1.

Addition of TSP-1 to a dynamic fibroblast cell culture surprisingly has no effect on apoptosis, in contrast to static culture (example 5). This shows that apoptosis depends not only on the production of TSP-1 but, on the contrary, also on the occurrence or accessibility of specific receptors on the surface of the cells. It was surprisingly possible to show in this connection that the integrin $\alpha_v\beta_3$ receptor is detectable on statically and dynamically cultivated cells, whereas the IAP receptor is expressed in detectable quantities only in static culture.

It is known that TSP-1 binds to the integrin $\alpha_v\beta_3$. The binding of TSP-1 to the $\alpha_v\beta_3$ integrin is mediated by an RGD sequence motif. A cyclic RGD peptide which binds to the $\alpha_v\beta_3$ integrin is marketed by Bachem Biochemica GmbH, Heidelberg, Germany.

A further possible interaction of TSP-1 with a receptor on fibroblasts is binding to IAP via the C-terminal cell-binding domain (CBD). The C-terminal cell-binding domain (CBD) is a domain of TSP-1 which interacts specifically with IAP. A truncated TSP-1 which consists only of this C-terminal cell-binding domain and binds to IAP is marketed by Bachem Biochemica GmbH, Heidelberg, Germany, as CBD peptide.

Addition of the CBD peptide and of the cyclic RGD peptide surprisingly led to a marked increase in the rate of apoptosis, which was at a similar level to the increase in the rate of apoptosis by addition of TSP-1 (example 7). It follows from this that only combined giving of both peptides to IAP and the integrin $\alpha_v\beta_3$ is effective for apoptosis.

It was thus possible to show, surprisingly, that the activity of TSP-1 for inducing spontaneous apoptosis is mediated exclusively via the binding to IAP and $\alpha_v\beta_3$ (example 10).

Since fibroblasts are not normally exposed to liquid flows in the in vivo situation, the inventors named previously have further investigated whether other mechanical forces are also able to inhibit the self-induced apoptosis of fibroblasts.

Corresponding investigations were carried out on fibroblasts cultured on collagen gels which had been isometrically contracted with ascorbic acid (example 11). It was surprisingly found in this case that cultivation under tension inhibits spontaneous apoptosis. It was additionally found, surprisingly, that relaxation of such fibroblasts cultivated with application of mechanical tension leads to a very marked increase in the rate of apoptosis of the fibroblasts (example 12). The results achieved with addition of thrombospondin-1, anti-TSP1 and anti-receptor antibodies support these findings and clearly show that, surprisingly, the application of mechanical tension inhibits apoptosis, exactly like dynamic cultivation. The corresponding results are shown in example 13.

In order to preclude an effect of the collagen used and of the ascorbic acid used, all the corresponding investigations were also carried out with cells cultivated on contractile silicone sheets (cultivation in the stretching apparatus, examples 16 and 17). It was additionally possible to preserve the mechanical tension by freezing the actin fibers of the cytoskeleton in previously tensioned cells with chondramide A (example 14) (chondramide A is an inhibitor of the depolymerization of F-actin). Expression of the proteins IAP and $\alpha_v\beta_3$ as a function of mechanical force (examples 15 and 18) was investigated in immunochemical investigations. It was shown that the expression of IAP correlates with the induction of apoptosis.

The aforementioned inventors were able by the investigations described above to show for the first time here that mechanical forces on their own are sufficient for regulating apoptosis. The underlying molecular mechanisms were discovered for the first time by the aforementioned inventors.

Surprisingly, and in an entirely unpredictable manner, it is therefore possible to employ substances usable according to the invention in order to ensure a particularly good result of wound healing.

In addition, substances usable according to the invention and mechanical forces can be employed in combination in order to ensure a particularly good result of wound healing.

This is because the presented results show that the actual cause of the induction of apoptosis is the absence of mechanical forces acting on the cells, the nature of these forces being immaterial. This causes the fibroblasts to secrete TSP-1, subsequently leading to the induction of apoptosis through the interaction with the integrin $\alpha_v\beta_3$ and IAP. The decrease in the fibroblast population (and other cells) leads to the progress of healing being retarded or absent.

For the purposes of the present invention, the apoptosis rate means the proportion of apoptotic cells in the total number of cells. A substance usable according to the invention is regarded as having anti-apoptotic activity if it is possible by using it in the cell culture to reduce the rate of apoptosis, compared with a cultivation carried out under identical conditions but without addition of precisely this substance, by 10%, preferably by at least 50%, particularly by at least 75% and very particularly preferably by at least 90%.

Such substances can be identified by:
(i) culturing cells which express both IAP and the integrin $\alpha_v\beta_3$,
(ii) causing the cells to produce an apoptosis-inducing substance, and/or adding a substance or substances inducing apoptosis,
(iii) adding the test substance,
(iv) measuring the rate of apoptosis, and
(v) selecting those substances whose addition to the cell culture results in a reduced rate of apoptosis, To carry out the corresponding experiments, the cells are cultivated in the suitable culture media in suitable cell culture vessels. These are normally standard media generally known in the prior art. For example, the cells are cultivated in DMEM, M-199, IF basal media etc. Suitable culture media are now available for virtually all cells and cell lines. Growth factors and hormones such as, for example, fetal calf serum (FCS) can be added to the culture medium before starting the culture. Mammalian cells are usually cultivated at 37° C. in a 5% $CO_2$ atmosphere which, in connection with the buffers used in the cell culture media, e.g. sodium carbonate buffers, makes it possible to stabilize the pH of the cell culture medium. A further possibility is to add to the cell culture media, before starting the cultivation, antibiotics which interact specifically with prokaryotic contaminating microorganisms and inhibit their growth, but leave the growth of the eukaryotic cells virtually unaffected and thus protect the cell culture from contamination. Further hints and information for cell culturing can be found in standard works, e.g. Zell- und Gewebekultur, 3rd edition, Toni Lindl, Jörg Bauer, (1994), Gustav Fischer Verlag.

Suitable culture conditions for cultivating fibroblasts are indicated in example 1.

Apoptosis mediators can be added to the cell culture for induction or increasing the rate of apoptosis.

This is because the spontaneous rate of apoptosis in a static cell culture is relatively low compared with rates of apoptosis induced by mediators such as TNF-α. The rates of apoptosis reached at the spontaneous rate of apoptosis induced by the static cell culture condition are in the range from 0.5% to 12% of the total cells. In the case of apoptosis induced by mediators, rates of apoptosis of up to 100% may be reached.

These mediators are hormones and other substances having apoptotic activity. These mediators are added in dissolved form to the cell culture, and it should be noted that the solutions used must be sterile. The sterility of the solutions can be achieved in various ways, preferably by heat treatment (autoclaving at 2 bar and 120° C.) or, if this method is unsuitable because of a particular sensitivity of the mediator to heat, by sterilizing filtration, for example using Nalgene disposable sterilizing filters. Methods of this type for sterilizing additions to cell culture are well known to the skilled worker.

The added test substances are preferably monoclonal antibodies, antibody fragments, polyclonal antibodies and peptides. Further preferred substances which can be investigated as test substances in the test system of the invention are low molecular weight compounds. Such compounds often have only slight or no side effects if they are employed as active principle in a pharmaceutical composition. A further advantage of such substances is the possibility of oral administration. However, it is also possible to add other substances suspected of being able to display an anti-apoptotic effect. These substances are preferably administered in dissolved form. The solvents in this case must be compatible with the cell culture. These test substances are therefore preferably dissolved in buffer solutions which have generally become widely used in cell culture. Examples thereof are phosphate buffers, sodium carbonate buffers and others. The dissolved test substances are preferably sterilized by filtration (sterilized) by sterilizing filtration (Nalgene disposable sterilizing filters) before addition to the cell culture in order to remove contaminating microorganisms or spores of fungi and undissolved constituents.

The dissolved test substance is preferably equilibrated, i.e. adjusted to the temperature of the cell culture, before addition to the cell culture. The volumes depend on the concentration which is to be reached of the test substance employed, and the volumes are preferably small so that no dilution effects occur in the cell culture media. The methods which can be used to introduce such test substances into cell cultures, preferably in the dissolved state, are well known to the skilled worker.

The decrease in the rate of apoptosis can be determined by any suitable measurement method. The methods described in DE 199 52 960.4 can preferably be employed for the present purposes. A particularly suitable early indicator is measurement of the nonappearance of the calcium influx into the cell through use of intra-cellular calcium indicators (see example 4). A method suitable for determining the exact rates of apoptosis is staining of the DNA of apoptotic cells and subsequent morphometric cell nucleus analysis or analysis of the cellular DNA content in a flow cytometer. An example of a suitable fluorescent dye is DAPI. These methods are well known in the art and are generally used for detecting apoptotic cells. If the number of apoptotic cells decreases after the use of a potential inhibitor of apoptosis by more than 10%, preferably more than 50%, particularly preferably by more than 75%, and very particularly preferably by more than 90%, based on the number of apoptotic cells in the test system in static culture, where appropriate after addition of an apoptosis-inducing substance, then this substance is regarded according to the invention as an inhibitor of apoptosis in the cells used. The non-appearance of the calcium influx into the cell can be used as an early indicator for screening purposes. Substances which lead to nonappearance of the calcium influx must subsequently be checked for their effect on apoptosis inhibition by DAPI staining (see example 4).

It is also possible to use other DNA dyes (e.g. Hoechst 33258) or conventional methods such as the Tunel assay (Tdt-mediated XdUTP nick end labeling; DNA breaks), the detection of apoptotic enzymes (e.g. PARP, caspases) or proteins (e.g. p53, CD95), the translocation of phosphatidylserine with fluorescent annexin or the detection of the DNA ladder in an agarose gel.

It is possible with the disclosed method to find substances having anti-apoptotic activity. These are preferably compounds which bind either to receptors on the cell surface, particularly preferably IAP and/or the integrin $\alpha_v\beta_3$ or to humoral factors, particularly preferably TSP-1, in such a way that the specific interaction described herein between TSP-1 and IAP and $\alpha_v\beta_3$, which leads to induction of apoptosis, does not take place, so that apoptosis cannot be induced and thus does not occur.

In a further preferred embodiment, these substances bind to IAP and thus prevent the apoptosis-specific calcium influx into the cell, so that apoptosis cannot be induced and thus does not occur.

These inhibitors are suitable for producing pharmaceutical preparations which can be used in wound treatment for suppressing apoptosis of fibroblasts, epithelial cells and other cells (e.g. smooth muscle cells).

Active substances to be tested with the method of the invention are, in particular, monoclonal antibodies and peptides which can easily be obtained with conventional methods of molecular biology and genetic manipulation. However, it is clear that other substances having a corresponding effect can also be found using the test system of the invention. The term "antibody" is used herein to describe both complete antibodies (i.e. antibodies having two heavy and two light chains) and fragments of antibodies having at least one antigen-binding site. The identification of an anti-TSP-1 antibody which has anti-apoptotic activity on fibro-blasts is described in example 6. Many other antibodies or antibody fragments can be tested in a similar way in order to prevent the induction of apoptosis.

It is clear that it is possible to produce a whole series of peptides and antibodies (antibody fragments) which can be identified as having anti-apoptotic activity using the method of the invention in a similar way. In addition, it is also possible to identify other substances which are not antibodies (antibody fragments) or peptides as having anti-apoptotic activity with the aid of the method of the invention.

For the purposes of the present invention, the term "peptide" means a substance which consists of one or more chains of a plurality, i.e. 2 or more, amino acids connected by peptide linkages.

For the purposes of the present invention, the term "protein" means a substance in which a plurality of "peptides" are connected together by peptide linkages. This definition encompasses equally native proteins and proteins which are at least partly "artificial", and such "artificial" proteins can be modified for example by attachment of chemical radicals which do not normally occur in native proteins to the amino acid chain.

For the purposes of the present invention, a peptide library means a collection of different peptides which can be investigated without further technical effort by the skilled worker for particular, specific binding properties. Particularly well known to the skilled worker and technically extremely simple to manipulate are, for example, peptide libraries based on the so-called phage display technology, in which up to $10^7$ and more phage particles each of which specifically express a particular peptide on their surface may be present in a few milliliters of test liquid. If such phage particles are subjected to enrichment by affinity chromatography, a biological factory for production, namely a monoclonal phage particle, i.e. an expression system, is also supplied at the same time as the specifically binding peptides. Such systems are extremely well known to the skilled worker.

However, native peptides often show a low metabolic stability in relation to peptidases and a relatively poor bioavailability.

Starting from the peptides shown above, the skilled worker is able without inventive effort to develop a whole series of derived compounds which have a similar or identical mode of action and which are also called inter alia peptidomimetics.

Compounds referred to as peptidomimetics for the purposes of the present invention are those which mimic the structure of peptides and are able as ligands to imitate (agonist) or to block (antagonist) the biological activity at the receptor/enzyme level. Peptido-mimetics ought in particular to have an improved bioavailability and have improved metabolic stability. The nature of the mimesis may range from a slightly modified initial structure up to a pure nonpeptide. See, for example, A. Adang et al., Recl. Trav. Chim. Pays-Bas 113 (1994), 63-78.

The possibilities available in principle for mimesis/derivatization of a peptide structure are as follows:
 use of D- in place of L-amino acids
 modification of the side chain of amino acids
 modification/extension of the main peptide chain
 cyclization to stabilize the conformation
 use of templates which impose a particular secondary structure Whereas the proteolytic stability of a peptide can be increased by replacing L- by D-amino acids, modification of the side chains of one of the amino acids often leads to an improvement in the binding properties of the complete peptide.

When the peptide backbond is modified there is usually replacement of an amide group by amide-like groups (J. Gante, Angew. Chem. 106 (1994), 1780-1802). It is possible by these measures to influence both the binding affinity and the metabolic stability of the native peptide.

Cyclization of a linear peptide fixes its flexibility and thus its global conformation. On fixation of the biologically active conformation, the affinity of the peptide for the receptor is increased because the decrease in entropion binding is less than on binding of a flexible linear peptide. For this purpose, amino acid side chains not involved in receptor recognition are linked together or to the peptide fragment.

The secondary structure of the peptide plays a crucial part in the molecular recognition of the receptor. Besides $\alpha$-helix and $\beta$-pleated sheet, important conformational elements are so-called turns as turning points in the peptide chain. Replacement of these structural units by a unit which stabilizes a definite secondary structure after insertion into a peptide has led to the concept of the secondary structure mimetic.

It is also possible to increase the solubility of the peptides in water for example by introducing S- and C-glycopeptide derivatives. Further measures may be, for example, PEGylation of the peptides.

The lipophilicity of hexapeptides can also be increased by, for example, attaching phenylalanines to the peptide sequence.

The cyclization and the N-terminal modification of peptides is described for example by Borchard, Journal of controlled Release 62 (1999), 231-238 and by Blackwell et al., J. Org. Chem. 10 (2001), 5291-302.

It is therefore clear that the skilled worker is able, starting from the knowledge provided by the present invention, easily to obtain a whole series of derived peptidomimetics, all of which are also encompassed by the present invention, however.

In a further preferred aspect, the present invention therefore provides peptidomimetics which are derived from SEQ ID Nos 1-11, and substances which comprise such peptidomimetics.

Particularly preferred substances usable according to the invention are low molecular weight compounds. Such compounds often have only slight or no side effects if they are employed as active principle in a pharmaceutical composition. A further advantage of such substances is the possibility of oral administration.

Examples thereof are cyclic pentapeptides as described by Haubner et al., J. Am. Chem. Soc. 1996, 118, 7641-7472. Low molecular weight substances include according to the invention small peptides, amino acids and amino acid analogs, steroids, nucleotides and other organic chemical substances having a molecular weight of $\leq 5\,000$, preferably $\leq 3\,000$ and particularly preferably $\leq 2\,000$. [Haubner, R., Gratias, R., Diefenbach, B., Goodman, S. L., Jonczyk, A., Kessier, II., *Structural and Functional Aspects of RGD-Containing Cyclic Pentapeptides as Highly Potent and Selective Integrin $\alpha_v\beta_3$ Antagonists*, 118, 7461-7462 (1996)].

Combinatorial libraries are likewise well known to the skilled worker. A large number of such libraries comprising a very large number of very different molecules exist. It is possible to obtain from these libraries in automated processes low molecular weight compounds which bind very specifically, and it is clear that it is easily possible, in the light of the invention presented here, to generate corresponding identificates usable according to the invention.

Corresponding products are produced by conventional methods. For example, it is possible to dissolve peptides or antibodies (antibody fragments), which are active ingredients of a pharmaceutical preparation, in a pharmaceutically acceptable carrier. One example of a pharmaceutically acceptable carrier may be buffer solutions such as phosphate buffers or citrate buffers. It is also possible to maintain the activity of the peptides by adding reagents which are pharmaceutically acceptable and, for example, maintain a reducing environment in the pharmaceutical preparation.

The specific dosage and posology for each patient depends on a number of factors, including the activity of the specific compounds used, the age of the patient, the bodyweight, the general state of health, the sex, the diet, the time of administration, the route of administration, the rate of excretion, the combination with other medicaments and the severity of the individual disorder for which the therapy is applied. It will be established by a physician as a function of these factors.

Polypeptide medicaments, e.g. protein medicaments or antibody medicaments, are normally administered parenterally, e.g. by an inhalation spray, rectally, by subcutaneous, intravenous, intramuscular, intra-articular and intrathecal injection and infusion techniques, or externally in pharmaceutical formulations which comprise conventional pharmaceutically acceptable carriers, adjuvants and vehicles. Other routes of administration are also suitable depending on the nature of the identified substance, e.g. orally.

The invention likewise provides pharmaceutical compositions which comprise an effective amount of a substance having anti-apoptotic activity in combination with a conventional pharmaceutical carrier. A pharmaceutical carrier is, for example, a solid or liquid filler, an encapsulating material or a solvent. Examples of materials which can be used as pharmaceutical carriers are sugars such as lactose, glucose and sucrose; starch such as corn starch and potato starch; cellulose and derivatives thereof such as sodium carboxymethylcellulose, ethylcellulose and cellulose acetate; powdered tragacanth; malt; gelatin; tallow; medicament carriers such as cocoa butter and suppository waxes; oils such as peanut oil, cottonseed oil, sunflower oil, sesame oil, olive oil, corn oil and soybean oil; polyols such as propylene glycol, glycerol, sorbitol, mannitol and polyethylene glycol; esters such as ethyl oleate and ethyl laureate; agar; buffering agents such as magnesium hydroxide and aluminum hydroxide; alginic acid; pyrogen-free water; isotonic saline; Ringer's solution, ethyl alcohol and phosphate buffer solutions, as well as other non-toxic compatible substances which are used in pharmaceutical formulations. Washing agents, emulsifiers and glidants such as sodium lauryl sulfate and magnesium stearate, as well as coloring agents, glidants, coating agents and perfuming agents and preservatives may likewise be present in the preparations according to the requirements of the pharmaceutical technologist. The amount of the active ingredient combined with the carrier materials in order to produce a single dose will vary depending on the treated patient and the specific method of administration. One example of such a pharmaceutical formulation is shown in example 19.

Production of a so-called living skin is described with great accuracy for example in the applications EP 1 005 873 and WO 99/43787 of Advanced Tissue Sciences Inc., and the skilled worker is familiar with it. It is possible to use for the purposes of the present invention artificial skin of whatever type if autologous or heterologous skin cells which express CD47 or $\alpha_v\beta_3$ on their surface are cultivated thereon, and if the matrix carrying the skin is stretchable.

EXAMPLES

The following examples explain the invention in more detail. However, they are not intended to be understood as restrictive.

ABBREVIATIONS

| Abbreviations | |
|---|---|
| IAP: | integrin-associated protein (CD 47) |
| CBD: | C terminal cell-binding domain of TSP-1 |
| TSP-1: | thrombospondin 1 |
| RGD: | Arg-Gly-Asp |
| HUVEC: | human umbilical vein endothelial cells |
| HPEC: | human placental endothelial cells |
| DAPI: | 4',6'-diamidino-2-phenylindole |
| MRC-5 | fibroblast cell line |
| Milli-Q | purified water |
| TNF-α | tumor necrosis factor alpha |
| bFGF | basic fibroblast growth factor |

EXAMPLE 1

Figure 1:
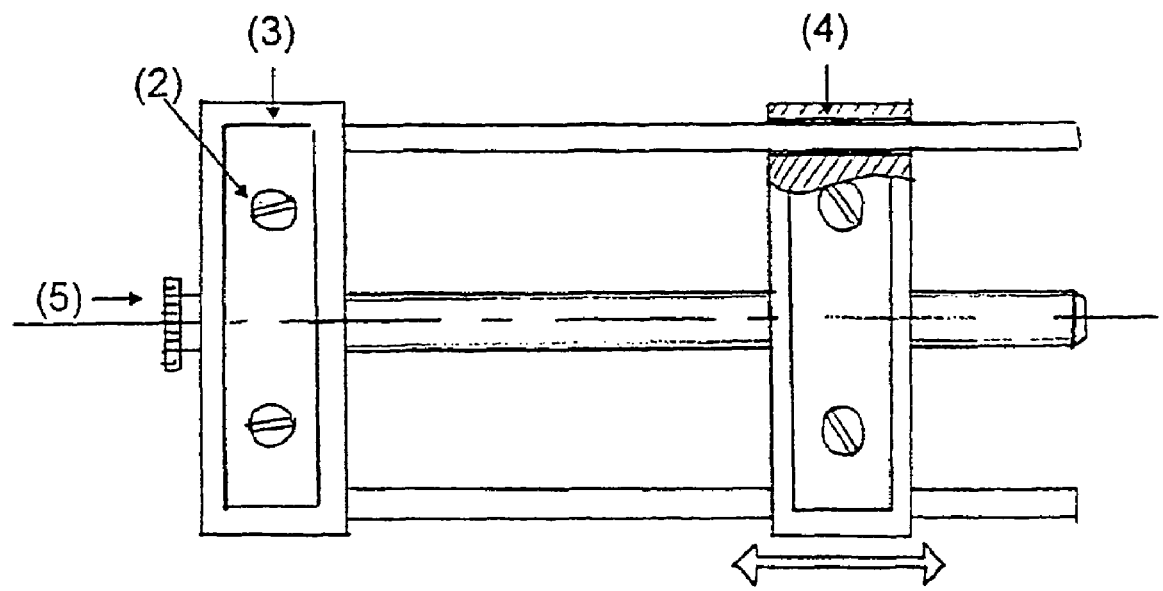
FIG. 1: stretching apparatus, top view

Cultivation of MRC-5 Fibroblasts (ATCC No.: CCL-171)

A) Reagents and Antibodies Used:

The RGD peptides, the CBD peptide and the Tsp1 are used as indicated in the following table:

| Ligand | Concentration | Incubation time | Biological activity |
|---|---|---|---|
| Human thrombospondin 1 Prof. Dr. Vischer, Universität Münster, Institut für Artheriosklereoseforschung | 1 µg/ml | (2–)24–72 h | binds integrin $\alpha_v\beta_3$ and IAP |
| RGD cyclic Bachem Biochemica GmbH, Heidelberg, Germany Catalog No. H25740 | 250 µg/ml | (2–)24–72 h | binds integrin $\alpha_v\beta_3$ |
| IAP peptide (CBD) Bachem Biochemica GmbH, Heidelberg, Germany Catalog No. H1418 | 400 µg/ml | (2–)24–72 h | binds IAP |

Specific Antibodies:
1.) Mouse monoclonal antibody against human CD47, from Cymbus Biotechnology Ltd, UK, Catalog No.: CBL 489, 50 µg/ml.
2.) Monoclonal and polyclonal antibody against Tsp1, from Prof. Dr. Vischer, Universität Münster, Institut für Artherioskleroseforschung, Germany, 50 µg/ml.
3.) Monoclonal antibody against the integrin $\alpha_v$ subunit, Chemicon International Inc., Canada, Catalog No.: MAB1960, 50 µg/ml.

B) Static, Dynamic and Tensioned Cultivation of MRC-5 Fibroblasts

Culture Medium for MRC-5:
89 ml of IF basal medium
10 ml of FCS (fetal calf serum)
1 ml of L-glutamine stock solution
IF Basal Medium
The IF basal medium is a 1:1 mixture of IMDM (Iscove's modified Dulbecco's medium) and Ham's F12 medium.
L-glutamine Stock Solution
200 mM L-glutamine are dissolved in IF basal medium and sterilized by filtration.

B1) Static Cultivation (Without Flow Stresses in the Cell Culture Medium):

The MRC-5 cell line used is seeded in ungelatinized cell culture vessels. The subsequent cultivation takes place in an incubator at 37° C. and 5% by vol. $CO_2$ in a water vapor-saturated atmosphere. The culture medium is changed every second to third day and, after confluence is reached, the cells are passaged with a division rate from 1:5 to 1:10.

B2) Dynamic Cultivation (Shear Stresses in the Cell Culture Medium):

The fibroblasts are initially cultivated under static conditions until confluence is reached. This is followed by cultivation under dynamic conditions in the cone and plate shear apparatus (after Bussolori et al. (1982) Rev. Sci. Instrum. 53, 1851-1854) for 24 h.

This is done by precultivation of the cells initially in gelatinized culture dishes (○=35 mm) with 0.15 ml/cm² culture medium and then further cultivation under turbulent or laminar flow conditions in the cone and plate shear apparatus for a maximum of 24 h. The flow conditions result from the angle of the cone. The flow over the cells is turbulent at a cone angle of 5° and is laminar at a cone angle of 0.5°.

Solutions:
70% (v/v) ethanol
Culture medium for MRC-5 fibroblasts (see above)
Material:
Cone and plate shear apparatus (after Bussolori et al. (1982) Rev. Sci. Instrum. 53, 1851-1854)

The shear stress generated is calculated from:

$$\tau = \frac{\mu \cdot 2\pi \cdot U_{display}}{\alpha}$$

τ=shear stress [dyn/cm]
µ=viscosity of the medium at 37° C.
α=cone angle
$U_{display}$=speed of rotation displayed on the control element [rpm]

Procedure:

Before use, the cone and plate shear apparatus is cleaned with a soft cloth and 70% (v/v) ethanol, the cone is sterilized and the apparatus is equilibrated at 37° C. in a heating cabinet. The precultivated cells are washed with basal medium and provided with 0.1 ml/cm² fresh culture medium, and the culture dish is rapidly fitted into the apparatus.

The cone is raised using the coarse adjustment, and the culture dish together with lid is inserted into the holder provided therefor. The lid is removed and the cone is adjusted over the culture dish. The exact distance of the plate cone tip from the cell lawn is adjusted using a micrometer screw.

The scale of the micrometer screw shows in this case a value of 175. At this value, which was previously found empirically, the cone tip rotates at a minimal distance from the cell lawn without abrading the latter. The assembled cone and plate shear apparatus is placed in the incubator at 37° C., 5% (v/v) $CO_2$ and water vapor-saturated atmosphere for the laminar or turbulent cultivation.

MRC-5 conditioned medium is produced as shown in Example 2.

B3) Cultivation in the Stretching Apparatus (Own Construction, FIGS. 1 and 2):

The cells are precultivated initially on gelatinized silicone sheets (1) and, two days after confluence is reached, cultivated further in the stretching apparatus for the desired period.

Solutions:
Culture medium for MRC-5 fibroblasts (see above)
Material:
Stretching apparatus, cell culture dishes (diameter: 147 mm) hexagon key, straight edge with millimeter scale, silcone sheet of types LP 500-1, LP 500-3, LP 500-5; manufactured by Laboratoire Perouse Implant, Bornel (France), marketed by Aromando Medizintechnik GmbH, Düsseldorf, Germany Procedure:

The stretching apparatus is initially cleaned with a soft cloth and 70% (v/v) ethanol and sterilized by autoclaving at 121° C. and 2 bar for 20 min in a saturated water vapor atmosphere.

The sterile stretching apparatus is then placed in a cell culture dish (⌀=147 mm) in such a way that the screws (2) which serve to fix the silicone sheet (1) point upward. The silicone sheet is introduced using forceps into the holder (3, 4) provided therefor and is fixed therein by tightening the screws of the holder (3, 4). The apparatus is turned through 180° round its horizontal axis.

The sheet is tensioned by the required length through turning the pitch screw (5), and the change in length is followed with the aid of a straight edge placed underneath the culture dish. Finally, 60 ml of culture medium are put in the culture dish. The assembled stretching apparatus is placed in the incubator at 37° C., 5% (v/v) $CO_2$ and water vapor-saturated atmosphere to cultivate the cells.

Figure 2:
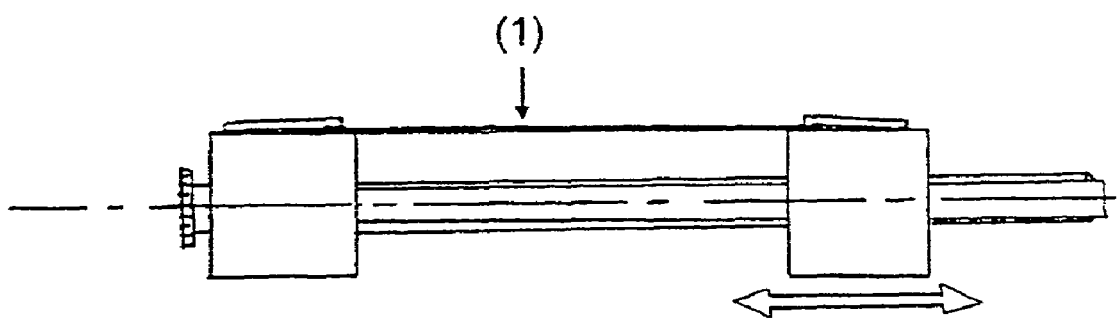
FIG. 2: stretching apparatus, side view

Cultivation in the Pulsatile Stretching Apparatus (Own Construction, see FIG. 11):

The cells are stretched/compressed with a frequency of 1 Hz in the pulsatile stretching apparatus. This is achieved by a cone, which is actuated by a processor-controlled electric motor, actuating the fastenings of the silicone sheet as shown in FIG. 1 or 2 with an appropriate speed. The cells are initially precultivated on gelatinized silicone sheets and, two days after confluence is reached, cultivated further in the pulsatile stretching apparatus for the desired period.

Solutions:
Culture medium for MRC-5 fibroblasts (see above)
Material:
Pulsatile stretching apparatus, cell culture dishes (diameter: 93 mm) hexagon key, straight edge with millimeter scale
Procedure:

The pulsatile stretching apparatus is initially cleaned with a soft cloth and 70% (v/v) ethanol. The component into which the silicone sheet is clamped is sterilized by autoclaving at 121° C., 2 bar for 20 min in a water vapor-saturated atmosphere and placed in a cell culture dish (⌀=93 mm) so that the screws which serve to fix the silicone sheet point upward. The silicone sheet is introduced by means of forceps into the holder provided therefor and fixed in the latter by tightening the screws of the holder. The apparatus is rotated by 180° around its horizontal axis, and 15 ml of culture medium are added.

The cell culture dish is then inserted into the holder provided therefor. The lid is removed, the eccentric is adjusted, and the speed of 1 Hz is set on the drive motor. The assembled stretching apparatus is placed in the incubator at 37° C., 5% (v/v) $CO_2$ and water vapor-saturated atmosphere to cultivate the cells.

EXAMPLE 2

Production of Conditioned Medium

Solutions:
Culture medium for MRC-5 fibroblasts (see above)
Materials:
MRC-5 confluent
Greiner tubes
Procedure:

IF basal medium from example 1 is put onto a confluent MRC-5 cell lawn and conditioned for 48 hours-72 hours. The conditioned medium is then centrifuged at 1000 $g_{av}$ for 5 minutes. The conditioned medium is frozen at −20° C. until used. The conditioned IF basal medium is employed for apoptosis investigations. For this purpose it can be supplemented anew with 2 mM glutamine.

EXAMPLE 3

Determination of the Rate of Apoptosis by DAPI Staining of Apoptotic Cells

DAPI belongs to the group of indole dyes and is a selective DNA dye. The dye is excited at 340-360 nm, and the emission maximum is at 480 nm. It is employed for apoptosis investigations [cf. Cohen et al., Immunology Today, 14, No. 3, 126-130, 1993)].

Morphological Evaluation:
Solutions:
PBS (Phosphate Buffered Saline):
140 mM NaCl, 3 mM KCl, 8 mM $Na_2HPO_4$ and 1.5 mM $KH_2PO_4$ are dissolved in water, with a pH of 7.2-7.4 being set up. The resulting solution is sterilized by autoclaving.
Formaldehyde Solution:
4% (v/v) formaldahyde in PBS
DAPI Solution:
30 nM DAPI (Molecular Probes, Leiden, Holland) in MeOH, stored at 4 C.
Materials:
Petri dish (35 mm) with MRC-5 fibroblasts in culture
Procedure:

The culture supernatant from a Petri dish is aspirated off, and the cell lawn is fixed with 1 ml of formaldehyde solution on ice for 15 minutes, washed twice with 2 ml of PBS, treated with 0.5 ml of DAPI solution for 15 minutes, washed with PBS and evaluated under the fluorescence microscope. The UV filter set and a 20× or 40× objective are used. 500-1 000 cells are selected at random, and the cells with apoptotic nuclei are counted.

The apoptosis index is calculated by the following formula:

$$\text{Apoptosis index } [\%] = \frac{\text{number of apoptotic cells}}{\text{total number of cells}} * 100$$

EXAMPLE 4

Measurement of the Induced Calcium Influx into the Cells by Using the Intracellular Calcium Indicator Fluo-3 AM Fluo-3 is a calcium indicator which forms a fluorescent complex after binding of $Ca^{2+}$. The ester Fluo-3 AM is taken up by the cell through diffusion. The calcium indicator Fluo 3 is produced in the cell only after hydrolysis of the ester. Extracellular dye ester therefore does not impair the measurement. The measurement is carried out with normal fluorescein filters. At an excitation wavelength of 488 nm (500 nm), the emission maximum is at 525 nm and is increased by a factor of 100 (200) through calcium binding. The measurement range is between 0.05 and 20 μM free $Ca^{2+}$ [Merritt, J. E. et al., Biochem. J. 269, 513-519 (1990)].

Solutions:
PBS (see above)
Culture medium for MRC-5 fibroblasts (see above)

6 mM Fluo-3 AM stock solution (50 μg in 10 μl dimethyl sulfoxide (DMSO); Molecular Probes, Leiden)
Fluo-3 AM concentration used: 3 μM in serum-free medium
Materials:
Cells in culture
24-well cell culture plates (microtiter plates)
Procedure:
Confluent MRC-5 cell lawns in 24-well plates are washed three times with serum-free medium, incubated with preheated serum-free medium with Fluo-3 AM under culture conditions for 30 minutes and washed three times, and the plate is measured with a fluorimeter. Firstly the sensitivity of the instrument is adjusted, and then fluorescence values corresponding to the instantaneous calcium level in the cell are recorded every 1-10 seconds. Substances can be added to the cells while the measurement is taking place. If a substance has an effect on the calcium level, this can be recognized from the increase or decrease in the fluorescence values. Assessment of the calcium level is possible with this method. The calcium influx is an early sign of apoptosis taking place.

EXAMPLE 5

Effect of Conditioned Medium on the Apoptosis of Statically and Dynamically Cultivated MRC-5 Fibroblasts Solutions and Specific Materials:
see example 1
Procedure:
The used culture medium from a confluent MRC-5 fibroblast culture is removed, and the cell lawn is washed once with culture medium and cultivated under the stated conditions for 24 h. The results obtained are listed in the following table.

| Cultivation | Culture medium | Apoptosis % |
|---|---|---|
| static | fresh | 2.8 ± 0.2 |
| static | conditioned | 5.1 ± 0.2 |
| dynamic | fresh | 0.5 ± 0.1 |
| dynamic | conditioned | 0.5 ± 0.1 |
| dynamic | fresh + TSP-1 | 0.4 ± 0.1 |

EXAMPLE 6

Effect of Thrombospondin-1 and Anti-Tsp1 Antibodies in the Culture Medium

Solutions and Specific Materials:
see example 1
Procedure:
The used culture medium from a confluent MRC-5 fibroblast culture is removed, and the cell lawn is washed once with culture medium and cultivated under the stated conditions for 24 h. The results obtained are listed in the following table.

| Culture medium | Apoptosis [%] |
|---|---|
| fresh | 1.6 ± 0.2 |
| fresh + Tsp1 | 5.6 ± 0.2 |
| conditioned | 5.1 ± 0.2 |
| fresh + polyclon. anti-Tsp1 | 0.6 ± 0.2 |
| conditioned + polyclon. anti-Tsp1 | 0.6 ± 0.2 |
| conditioned + monoclon. anti-Tsp1 | 0.6 ± 0.2 |

EXAMPLE 7

Change in the Apoptosis of MRC-5 Fibroblasts After Addition of Specific Peptides to the Culture Medium Solutions and Specific Materials:
see example 1
Procedure:
The used culture medium from a confluent MRC-5 fibroblast culture is removed, and the cell lawn is washed once with culture medium and cultivated under the stated conditions for 24 h. The results obtained are listed in the following table.

| Culture medium | Apoptosis [%] |
|---|---|
| fresh | 1.6 ± 0.2 |
| conditioned | 5.1 ± 0.2 |
| fresh + Tsp1 | 5.6 ± 0.2 |
| fresh + CBD + RGD/cycl. | 5.7 ± 0.3 |

EXAMPLE 8

Tsp1 Secretion Under Static and Dynamic Culture Conditions (24 h)

Procedure:
The used culture medium from an MRC-5 fibroblast culture 1 to 3 days post-confluence is removed, and the cell lawn is washed once with culture medium and cultivated under the stated conditions for 24 h. The resulting medium is removed and centrifuged at 1 000 $g_{av}$ at room temperature for 5 min, and the supernatant is used to determine the Tsp1 content. The number of cells in the particular culture is found. The results obtained are listed in the following table.

| Culture condition | Tsp1 [ng/1 × $10^6$ cells] |
|---|---|
| static | 53.5 ± 6.1 |
| dynamic | 10.9 ± 0.5 |

EXAMPLE 9

Tsp1 Secretion Under Static Conditions as a Function of the Duration of Cultivation Procedure:
The used culture medium from a confluent culture is removed, and the cell lawn is washed once with culture medium and cultivated further under static conditions. The resulting medium is removed and centrifuged at 1000 $g_{av}$ at room temperature for 5 min, and the supernatant is used to determine the Tsp1 content. The number of cells in the particular culture is found. The results obtained are listed in the following table.

| Days, post confluence | Tsp1 [ng/1 × $10^6$ cells] |
|---|---|
| 1 | 7.8 ± 3.0 |
| 2 | 19.1 ± 2.5 |
| 3 | 21.2 ± 3.7 |
| 4 | 39.7 ± 3.8 |
| 5 | 99.2 ± 19.7 |
| 6 | 179.6 ± 16.3 |
| 7 | 192.4 ± 18.0 |

EXAMPLE 10

Effect of Anti-receptor Antibodies

Solutions and specific materials:
see example 1
Procedure:
The used culture medium from a confluent culture is removed, and the cell lawn is washed once with culture medium and cultivated under the stated conditions for 24 h. The results obtained are listed in the following table.

| Culture medium | Apoptosis [%] |
|---|---|
| fresh | 1.6 ± 0.2 |
| conditioned | 5.1 ± 0.2 |
| conditioned + monoclon. anti-$\alpha_v$ | 0.5 ± 0.3 |
| conditioned + monoclon. anti-IAP | 0.3 ± 0.2 |

EXAMPLE 11

Generation of Mechanical Tension by Isometric Collagen Contraction in Fibroblast Cultures 1. Routine Cultivation, Two-Dimensional:
   Culture Medium:
   Culture medium for MRC-5 fibroblasts (see example 1)
   Procedure:
   The MRC-5 cell line used is seeded in ungelatinized cell culture vessels. The subsequent cultivation takes place in an incubator at 37° C. and 5% by vol. $CO_2$ in a water vapor-saturated atmosphere. The culture medium is changed every second to third day and, after confluence is reached, the cells are passaged with a division rate from 1:5 to 1:10.

2. Cultivation in Collagen Matrices, Three-Dimensional:
   The fibroblasts are initially cultivated under static conditions in 75 $cm^2$ cell culture bottles until confluence is reached. The cells are harvested using 0.05% (w/v) trypsin/0.02% (w/v) EDTA in PBS.

2A. Production of the Collagen Gel (3 mg/ml):
   Materials:
   Vitrogen "100" collagen, 4° C., from COHESION Technologies, INC., Palo Alto, Calif., USA
   10× concentrated PBS stock solution, pH =7.4, with 0.005 mg/ml phenol red
   0.1 M HCl
   0.1 M NaOH
   Procedure:
   The total volume is 2 ml per mixture: 0.2 ml of 10×PBS and 0.2 ml of 0.1 M NaOH are added to 1.6 ml of Vitrogen "100" and the pH is adjusted to 7.4 with 0.1 M HCl or 0.1 M NaOH.

2B. Cell Seeding in the Produced Collagen Gels:
   $2 \times 10^5$ cells are seeded in each collagen matrix. For this purpose, 100 µl of the cell suspension (the appropriate cell titer is adjusted after the trypsinization in serum-free DMEM) are introduced into 1.5 ml reaction vessels pre-equilibrated at 37° C., 100 µl of the neutralized collagen solution are added, and the resulting solution is incubated at 37° C. for 4 min. The collagen concentration is 1.5 mg/ml. The cell/collagen suspension is seeded in 24-well cell culture plates or in 3.5 cm culture dishes. The matrix is polymerized at 37° C. for 60 min.

2C. Generation of Mechanical Tension:
   Material:
   DMEM basal medium (Dulbecco's modified Eagel medium
   Ascorbic acid stock solution (100×)
      5 mg/ml ascorbic acid are dissolved in DMEM basal medium and sterilized by filtration
   Culture medium (tension) (per 100 ml)
      89 ml of DMEM basal medium
      10 ml of FCS
      1 ml of ascorbic acid stock solution
   Culture medium DMEM (per 100 ml)
      90 ml of DMEM basal medium
      10 ml of FCS
   Procedure:
   The matrices are covered with a layer of culture medium (DMEM+10% FCS+50 µg/ml ascorbic acid) and cultivated in an incubator at 37° C. and 8.5% by volume $CO_2$ in a water vapor-saturated air atmosphere for 24 h.
   Addition of ascorbic acid leads to an "isometric" contraction of the collagen matrix, thus generating the mechanical tension on the cells.
   The medium is changed after 24 h. Further cultivation takes place with DMEM+10% FCS (see above).

Cultivation of the Cells Under Mechanical Tension:
   The matrix remains adherent to the bottom of the culture vessel for the period stated in each case.

Cultivation of the Cells Under Relaxed Conditions:
   The adherent matrix is cautiously detached with a spatula from the substrate and "floats" in the culture medium without contact with the substrate. The tension is abolished. The cultivation takes place for the period stated in each case.

EXAMPLE 12

Effect of Mechanical Tension on the Apoptosis of MRC-5 Fibroblasts

Procedure:
   The cells are cultivated as stated in example 11. Day "0" corresponds to the time after 24 h cultivation with ascorbic acid-containing medium before further cultivation under tensioned or relaxed conditions. After the stated times, the cell/collagen matrix is fixed in 4% (w/v) paraformaldehyde in PBS, followed by DAPI staining. The results obtained are listed in the following table.

| Cultivation | Cultivation time | Apoptosis [%] |
|---|---|---|
| precultivation | day "zero", 0 h | 1.3 ± 0.2 |
| relaxed | 24 h | 10.2 ± 0.7 |
| relaxed | 48 h | 11.5 ± 0.5 |
| relaxed | 72 h | 11.2 ± 0.6 |
| tensioned | 24 h | 2.4 ± 0.2 |
| tensioned | 48 h | 1.7 ± 0.2 |
| tensioned | 72 h | 1.8 ± 0.3 |

EXAMPLE 13

Effect of Thrombospondin-1, of Anti-Tsp1 and Anti-Receptor Antibodies on the Tension-Dependent Apoptosis of MRC-5 Fibroblasts Substances and Antibodies Used:
Substances:
1. Purified Tsp1, from Dr. Vischer, Münster, Germany, 20 µg/ml.
2. Chondramide A, a cytostatic isolated from myxobacteria, from Prof. H. Reichenbach, GBF, Brunswick, Germany, 1 µM.

Specific Antibodies:
1. Mouse monoclonal antibody against human CD47, from Cymbus Biotechnology Ltd, UK, 50 µg/ml (see example 1)
2. Monoclonal and polyclonal antibody against Tsp1, from Dr. Vischer, Munster, Germany, 50 µg/ml.
3. Monoclonal antibody against the integrin β3 subunit, Chemicon International Inc., Canada, Catalog No.: MAB1957, 50 µg/ml.

Procedure:
The precultivation, including the generation of the mechanical tension, takes place as described in example 11. "0 h" corresponds to the time after 24 h cultivation with ascorbic acid-containing medium before further cultivation under tension and relaxed conditions and addition of the substances mentioned. The further cultivation time is 24 h. The results obtained are listed in the following table.

| Cultivation | Culture medium | Period | Apoptosis [%] |
|---|---|---|---|
| Precultivation | DMEM/FCS/ ascorbic acid | Day "zero", 0 h | 1.1 ± 0.2 |
| tensioned | DMEM/FCS | 24 h | 1.0 ± 0.2 |
| relaxed | DMEM/FCS | 24 h | 6.2 ± 0.2 |
| relaxed | DMEM/FCS + mAb IAP | 24 h | 0.5 ± 0.1 |
| relaxed | DMEM/FCS + mAb β3 | 24 h | 0.9 ± 0.2 |
| relaxed | DMEM/FCS + mAb Tsp1 | 24 h | 0.5 ± 0.1 |
| relaxed | DMEM/FCS + Tsp1 | 24 h | 10.5 ± 0.5 |

EXAMPLE 14

The Effect of Chondramide A on the Cytoskeleton of MRC-5 (Cultivation in Collagen Matrices)

Procedure:
The precultivation and tensioning with ascorbic acid-containing culture medium takes place as described in example 11. The procedure with the chondramide-containing sample is as follows: the ascorbic-containing medium is removed and incubated with 1 µM chondramide A in culture medium for 1 h. This is followed by detachment of the matrix from the substrate and a change of the culture medium. The further cultivation time of all mixtures is 8 h. The results obtained are listed in the following table.

| Cultivation | Culture medium | Period | Apoptosis (%) |
|---|---|---|---|
| tensioned | DMEM/FCS | 8 h | 0.9 ± 0.2 |
| relaxed | DMEM/FCS | 8 h | 2.7 ± 0.2 |
| relaxed | DMEM/FCS + chondramide A | 8 h | 1.0 ± 0.2 |

EXAMPLE 15

Immunochemical Detection of IAP and the Integrin β3 Subunit on MRC-5 Fibroblasts Under Various Culture Conditions Procedure:
The precultivation takes place as described in example 11 (routine cultivation, two-dimensional:). The further cultivation under tension and relaxed conditions takes place for 72 to 96 h.

Immunostaining:
removal of the culture medium
wash cell/collagen matrix 1× with PBS (37° C.)
fix 2% (w/v) paraformaldehyde in PBS at 4° C. for 30 min
The following steps are carried out on a Heidolph Duomax plate shaker (level 2) at room temperature.
2× in PBS for 5 min each time
saturate in 0.5% (v/v) Tween 20+0.5% (w/v) BSA in PBS for 1 h
wash 2× in 0.5% (v/v) Tween 20 in PBS for 5 min each time
incubation for 3 h with monoclonal mouse anti-human CD47 (Cymbus Biotechnology Ltd, UK, see example 1) or monoclonal mouse anti-human β3 antibody (Chemicon International Inc., Canada, Catalog No.: MAB1957), 1:100 in 0.5% (v/v) Tween 20 in PBS
wash 3× in 0.5% (v/v) Tween 20 in PBS for 5 min each time
The following steps are carried out with protection from light:
incubation for 2 h with Cy3™ conjugated F(ab)2 fragment from rabbit anti-mouse IgG (Dianova, Hamburg, Germany), wash 1:200 in 0.5% (v/v) Tween 20 in PBS
wash 3× in 0.5% (v/v) Tween 20 in PBS for 5 min each time.
cover collagen matrix with layer of PBS
fluorescence microscopic evaluation (FIG. 40×)
Note: two types of negative control are carried out:
a) in place of the specific CD47 antibody, nonspecific mouse IgG is used in the same concentration.
b) the cell lawn is incubated only with Cy3™ (Dianova, Hamburg, Germany) conjugated F(ab)$_2$ fragment.

All stained cells were positive for the integrin. IAP was detectable only on the cells cultivated under relaxed conditions. The cell cultivated under tensioned conditions show no IAP expression.

EXAMPLE 16

Figure 3:
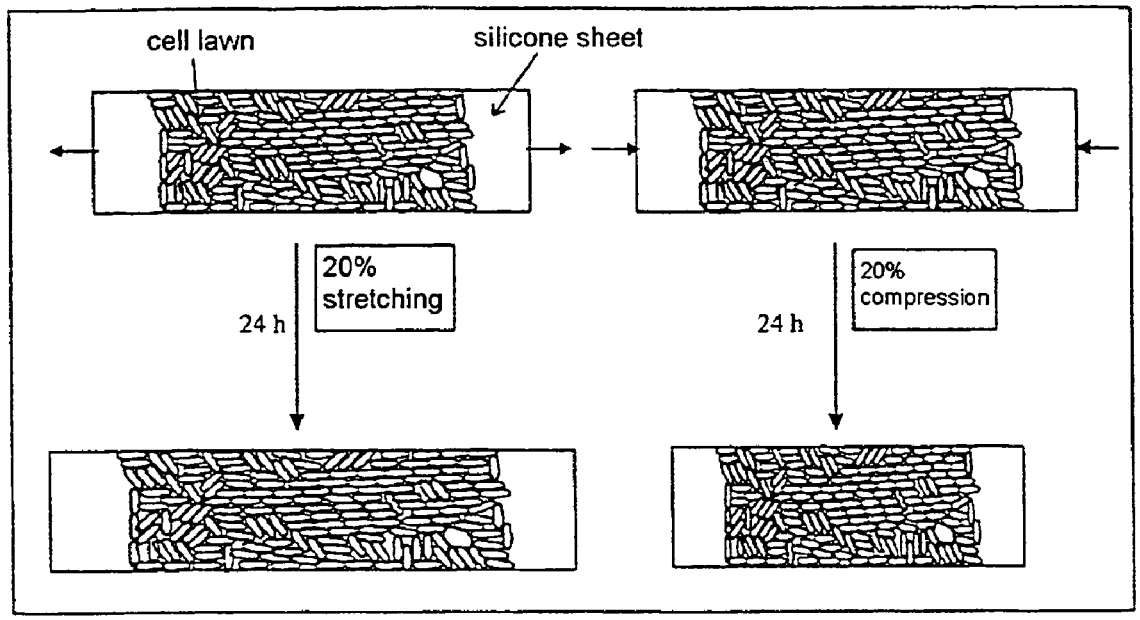
FIG. 3: diagrammatic mode of functioning of the stretching apparatus (Ex. 16)

Detection of the Effect of Extension and Compression of the Cells on the Apoptosis Index In order to be able to investigate the effect of mechanical forces resulting from the extension of the cells, cells are seeded on silicone sheets. One day after confluence is reached, the sheet is fitted in the stretching apparatus and extended by 20%. The apoptosis index is determined after incubation under culture conditions for 24 and 48 h. For compression of the cells, they are seeded on a sheet which has already been pretensioned. This sheet is relaxed by 20% one day after confluence is reached. This is shown diagrammatically in FIG. 3. Once again, the apoptosis index is determined after 24 and 48 h. The results are depicted in FIG. 4.

Figure 4:
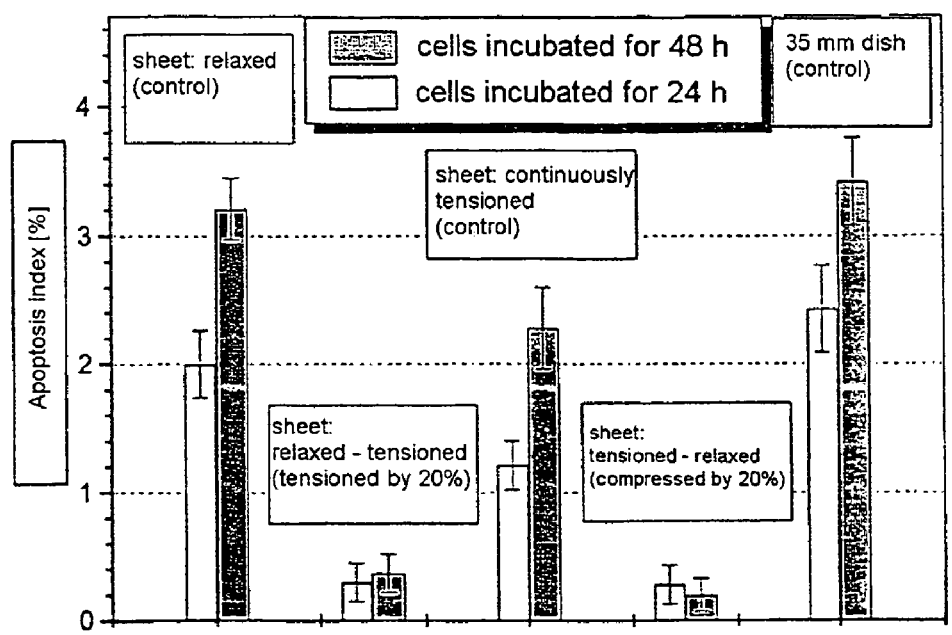
FIG. 4: determination of the effect of extension and compression of the cells on the apoptosis index (Ex. 16)

It is evident from FIG. 4 that the mechanical tension induced [lacuna] the cells by tensioning and relaxing the sheets has a marked effect on the apoptosis index. The apoptosis index is considerably lower both in the tensioned and in the compressed cells than in the controls. The comparatively low value of the tensioned sheet is noteworthy.

This can be explained by the material of the sheet allowing a slight relaxation over the cultivation period, resulting in a minimal compression of the cells which leads to a slight reduction in the apoptosis index. There is no significant difference evident between tensioning or compression for one day and two days.

EXAMPLE 17

Determination of the Effect of Extension of the Cells on the Proliferation and Apoptosis Index Measurement of the Proliferation Index:

The proliferation rate is used to quantify the number of proliferating cells obtained in an experiment. The definition of this is as follows:

$$PR\ [\%] = \frac{Z_{prolif}}{Z} \cdot 100$$

where PR=proliferation rates [%]
$Z_{prolif}$=number of proliferating cells
Z=total number of cells.

To measure the proliferation rate, the computer program "ZellCount" is used to count, in each of three experiments carried out independently of one another, a sufficient number of fields of view to reach a total number of 1 000 cells. The adjustment of the background is chosen so that both the living and the apoptotic cells are counted.

| Detection of proliferating cells by BrdU labeling: | |
|---|---|
| Solutions: | Proteins: |
| PBS | MAb BrdU |
| 70% ethanol | Monclonal mouse anti-BrdU IgG |
| 3N HCl | Concentration of the crude |
| BrdU/dC solution | fractions: |
| 15 mM BrdU + 15 mM dC in | 20-250 µg/ml |
| Milli-Q, | Working concentration: 0.25 µg/ml |
| store at −20° C. | in PBT-BSA |
| Working dilution: 1:1000 in | Mouse IgG |
| culture medium | Total protein content: 13.8 mg/ml |
| PBT | is sterilized by filtration after |
| PBS + 0.5% (v/v) Tween 20 | making up in PBT-BSA |
| PBT-BSA | Working concentration: 25 µg/ml |
| PBT + 0.5% (w/v) BSA | in PBT-BSA |
| DAPI solution | BT-KAM |
| 30 nM DAPI in methanol | biotinylated rabbit anti-mouse |
| | IgG |
| | Total protein content: 1.0 mg/ml |
| | Working dilution: 1:3000 in |
| | PBT-BSA |
| | Cys3 ™-SP |
| | Cy3 ™ conjugated streptavidin |
| | Concentration: 1.8 mg/ml |
| | Working conc.: 5 µg/ml in PBT-BSA |
| | Evaluation: Nikon Filterblock G |
| | Excitation wavelength: 553 nm. |
| | Emission wavelength: 575 mn. |

Procedure:

The cell lawn is incubated with 0.2 ml/cm² of the BrdU/dC solution diluted 1:1000 in culture medium for 30 min. The incubation is followed by washing twice with PBS, fixing the cell lawn with 0.2 ml/cm² 70% EtOH at 4° C. for 30 min and washing three times with PBS.

The following steps are carried out with gentle agitation (Duomax 1030, level 2) at room temperature:

The DNA is denatured by adding 0.2 ml/cm² 3N HCl for 20 min, which is followed by washing five times with PBS. 0.2 ml/cm² of the MAb-BrdU is added and agitated for 30 min. The labeling is followed by washing five times with PBT, adding 0.2 ml/cm² BT-Kam, incubating for 3 hours and washing a further five times with PBT for 3 minutes. Staining takes place by adding 0.2 ml/cm² Cy3-SP for one hour and is stopped by washing five times with PBT for 3 minutes each time. To determine the proliferation rate it is necessary to carry out a DAPI counterstain and to evaluate the specimens after covering the cell lawn with a layer of PBS under the fluorescence microscope.

A constant increase in the apoptosis and proliferation index is evident with the statically cultivated fibroblasts (FIG. 8).

EXAMPLE 18

Investigation of the Expression of the $\beta_3$ Subunit of the Integrin $\alpha_v\beta_3$ and of IAP Under Tensioned and Relaxed Culture Conditions One day after the tensioning of the silicone sheets, the MRC-5 are fixed and stained by means of indirect immunofluorescence staining in order to be able to characterize the expression of the $\beta_3$ subunit of the integrin $\alpha_v\beta_3$ and of IAP. The results of the stainings show that expression of IAP on fibroblasts stretched by 20% is weaker than in cells cultivated on the untensioned silicone sheet. This result is consistent with the previously measured apoptosis and proliferation indices.

EXAMPLE 19

Use of Antibodies or Peptides as Active Substances in Pharmaceutical Formulations The identified compounds having anti-apoptotic activity could be employed as active substances in pharmaceutical formulations for the treatment of traumatic conditions.

For this purpose, antibodies are expediently employed for example in a concentration of 3-5 mg per ml in the following formulation:
water for injections
Polysorbate 80
disodium hydrogen phosphate/sodium dihydrogen phosphate
sodium chloride This formulation is administered (sprayed on) as spray solution.

EXAMPLE 20

Incubation of Fibroblasts with Peptides Having Anti-apoptotic Activity

The cells are cultivated under static culture conditions as in example 1/variant 1B1. The cells are seeded in the appropriate culture vessels (e.g. 24-well plate/0.5 ml per well) and employed for the test 3 days after complete confluence is reached. The cells are provided with new medium:
(a) fresh culture medium [basic rate of apoptosis]
(b) fresh culture medium with 1 μg/ml TSP-1 [apoptosis-inducing substance; control]
(c) culture medium (b)+peptide of SEQ ID NO 1; 1 mM
(d) culture medium (b)+peptide of SEQ ID NO 2; 1 mM
(e) culture medium (b)+peptide of SEQ ID NO 3; 1 mM
(f) culture medium (b)+peptide of SEQ ID NO 4; 1 mM
(g) culture medium (b)+peptide of SEQ ID NO 7; 1 mM
(h) culture medium (b)+peptide of SEQ ID NO 8; 1 mM
(i) culture medium (b)+peptide of SEQ ID NO 9; 1 mM
(j) culture medium (b)+peptide of SEQ ID NO 10; 1 mM
(k) culture medium (b)+peptide of SEQ ID NO 11; 1 mM
(l) culture medium (b)+peptide of SEQ ID NO 5; 1 mM
(m) culture medium (b)+peptide of SEQ ID NO 6; 1 mM After incubation under culture conditions (example 1) for 24 h, the cells are fixed, stained with DAPI and examined morphologically under the fluorescence microscope. The apoptotic cells and the total number of cells are determined, and the apoptosis index is calculated (percent of apoptotic cells). The data from 3 independent experiments are indicated in the following table, indicating the averages and the standard deviation.

The following peptides are tested:

| SEQ ID NO | Amino acid sequence | Apoptosis index [%] | Inhibition index [%] |
|---|---|---|---|
| K | control | 4.23 ± 0.23 | |
| (1) | R-A-Y-V-V-M | 1.21 ± 0.29 | 71.4 ± 6.8 |
| (2) | R-W-Y-V-V-M | 2.00 ± 0.29 | 53.7 ± 6.8 |
| (3) | R-Y-Y-V-V-M | 1.45 ± 0.04 | 65.3 ± 0.9 |
| (4) | R-E-Y-V-V-M | 0.87 ± 0.32 | 80.4 ± 7.0 |
| (7) | R-G-Y-V-V-M | 2.00 ± 0.59 | 53.7 ± 13.9 |
| (8) | R-M-Y-V-V-M | 2.46 ± 0.29 | 42.8 ± 6.9 |
| (9) | R-T-Y-V-V-M | 3.19 ± 0.50 | 25.4 ± 11.8 |
| (10) | R-N-Y-V-V-M | 3.70 ± 1.11 | 13.5 ± 16.2 |
| (11) | R-D-Y-V-V-M | 2.66 ± 0.71 | 38.9 ± 16.7 |
| (5) | K-R-A-Y-V-V-M-W-K-K | 0.42 ± 0.21 | 90.1 ± 4.9 |
| (6) | K-R-E-Y-V-V-M-W-K-K | 0.24 ± 0.18 | 94.4 ± 4.2 |

K: no peptide employed

The apoptosis-inhibiting effect of these peptides is clearly evident, making them suitable for the use according to the invention for the treatment of wounds.

The inhibition index of the peptides employed is calculated as follows:

Inhibition index [%]=100−(measured apoptosis index* 100/control apoptosis index)

```
                        SEQUENCE LISTING

<160> NUMBER OF SEQ ID NOS: 11

<210> SEQ ID NO 1
<211> LENGTH: 6
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 1

ARG ALA TYR VAL VAL MET
1               5

<210> SEQ ID NO 2
<211> LENGTH: 6
<212> TYPE: PRT
<213> ORGANISM: ARTIFICIAL SEQUENCE
<220> FEATURE:
<223> OTHER INFORMATION: SYNTHETIC PEPTIDE
```

```
<400> SEQUENCE: 2

ARG TRP TYR VAL VAL MET
1               5

<210> SEQ ID NO 3
<211> LENGTH: 6
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 3

ARG TYR TYR VAL VAL MET
1               5

<210> SEQ ID NO 4
<211> LENGTH: 6
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 4

ARG GLU TYR VAL VAL MET
1               5

<210> SEQ ID NO 5
<211> LENGTH: 10
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 5

LYS ARG ALA TYR VAL VAL MET TRP LYS LYS
1               5                   10

<210> SEQ ID NO 6
<211> LENGTH: 10
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 6

LYS ARG GLU TYR VAL VAL MET TRP LYS LYS
1               5                   10

<210> SEQ ID NO 7
<211> LENGTH: 6
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 7

ARG GLY TYR VAL VAL MET
1               5

<210> SEQ ID NO 8
<211> LENGTH: 6
<212> TYPE: PRT
<213> ORGANISM: ARTIFICIAL SEQUENCE
<220> FEATURE:
<223> OTHER INFORMATION: SYNTHETIC PEPTIDE
```

```
-continued

<400> SEQUENCE: 8

ARG MET TYR VAL VAL MET
1               5

<210> SEQ ID NO 9
<211> LENGTH: 6
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 9

ARG THR TYR VAL VAL MET
1               5

<210> SEQ ID NO 10
<211> LENGTH: 6
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 10

ARG ASN TYR VAL VAL MET
1               5

<210> SEQ ID NO 11
<211> LENGTH: 6
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 11

ARG ASP TYR VAL VAL MET
1               5
```

The invention claimed is:

1. A medicament for promoting wound healing, comprising a substance that bind to at least one of integrin-associated protein (IAP), integrin $\alpha_v\beta_3$, and thrombospondin 1, wherein said substance inhibits binding between thrombospondin 1 and at least one of IAP and integrin $\alpha_v\beta_3$, and inhibit apoptosis characterized by nuclear fragmentation of cells, wherein said substance is a peptide consisting of the amino acid sequence depicted in SEQ ID NO 1.

2. The medicament of claim 1, wherein the substance binds to at least one of IAP and integrin $\alpha_v\beta_3$ on fibroblasts and/or to thrombospondin 1 in such a way that the binding between thrombospondin 1 and the at least one of IAP and integrin $\alpha_v\beta_3$ is inhibited and the rate of apoptosis of the cells is reduced by more than 10%.

3. The medicament of claim 2, wherein the cells are epithelial cells.

4. The medicament of claim 2, wherein the cells are keratinocytes.

5. The medicament of claim 1 prepared by carrying out an identification method comprising steps (i) to (v), as follows:
   (i) culturing cells which express both IAP and integrin $\alpha_v\beta_3$,
   (ii) causing the cells to produce an apoptosis-inducing material, and/or adding a material or materials inducing apoptosis,
   (iii) adding a substance,
   (iv) measuring the rate of apoptosis, and
   (v) selecting identificate substances which cause a reduced rate of apoptosis, and then
   mixing the identificates with a pharmaceutically acceptable carrier.

6. The medicament of claim 1, wherein the substance is a peptide selected from a peptide library by prescreening with affinity chromatography using at least one of thrombospondin 1, IAP, and integrin $\alpha_v\beta_3$ as a target.

7. The medicament of claim 1, wherein the substance is a low molecular weight active substance with a molecular weight of $\leq 5000$.

8. The medicament of claim 7, wherein the low molecular weight active substance is selected from a combinatorial library by prescreening with affinity chromatography using at least one of thrombospondin 1, IAP, and integrin $\alpha_v\beta_3$ as a target.

9. The medicament of claim 5, wherein the cells employed in the identification method are endothelial cells.

10. The medicament of claim 5, wherein the cells employed in the identification method are smooth muscle cells or fibroblasts.

11. The medicament of claim 5, wherein the cells employed in the identification method are genetically modified cells which express both IAP and $\alpha_v\beta_3$ on their surface.

12. The medicament of claim 5, wherein the cells employed in the identification method are cultivated under conditions under which consistently directed laminar flows do not occur.

13. The medicament of claim 5, wherein thrombospondin 1 or an analogous compound with identical binding properties is added to the cell culture in the identification method.

14. The medicament of claim 5, wherein the induction of apoptosis in the identification method is determined by measuring increased calcium influx into the cell.

15. The medicament of claim 5, wherein the rate of apoptosis in the identification method is determined by a method selected from the group consisting of DAPI staining, TUNEL assay, DNA ladder, annexin staining and enzyme detection.

16. The medicament of claim 5, wherein the identificates bind to a calcium channel in the cell membrane in such a way that apoptosis-specific calcium influx into the cells is suppressed.

17. The medicament of claim 5, wherein the identificates inhibit apoptosis-specific calcium influx into fibroblasts.

18. The medicament of claim 5, wherein the process comprises admixing at least one different fibroblast growth factor to the medicament in addition to the indentificates.

19. The medicament of claim 1, further comprising at least one fibroblast growth factor.

20. The medicament of claim 19, wherein the fibroblast growth factor is basic fibroblast growth factor.

21. The medicament of claim 1, further comprising a pharmaceutical acceptable carrier.

* * * * *

UNITED STATES PATENT AND TRADEMARK OFFICE
CERTIFICATE OF CORRECTION

PATENT NO. : 7,582,725 B2  Page 1 of 1
APPLICATION NO. : 10/469126
DATED : September 1, 2009
INVENTOR(S) : Mark A. Freyberg et al.

It is certified that error appears in the above-identified patent and that said Letters Patent is hereby corrected as shown below:

On the Title Page:

At field (73), "Dermatools" should be -- DermaTools --.
At field (57), line 4, "thrombuspondin-1" should be -- thrombospondin-1 --.
At field (57), line 5, "thrumbospondin-1" should be -- thrombospondin-1 --.

At Column 29, line 42, "bind" should be -- binds --.

Signed and Sealed this

Twenty-ninth Day of June, 2010

David J. Kappos
*Director of the United States Patent and Trademark Office*